US006953595B2

(12) United States Patent
Basic et al.

(10) Patent No.: US 6,953,595 B2
(45) Date of Patent: Oct. 11, 2005

(54) INHIBITORS OF APOPTOSIS OF NERVE CELLS

(76) Inventors: Robert Basic, Dubravica 30, Zagreb (HR), 10000; Milivoj Slijepcevic, Zmajevac 10, Zagreb (HR), 10000; Mirko Hadzija, G. Tadino 18, Zagreb (HR), 10000; Marijana Hadzija, G. Tadino 18, Zagreb (HR), 10000

( * ) Notice: Subject to any disclaimer, the term of this patent is extended or adjusted under 35 U.S.C. 154(b) by 0 days.

(21) Appl. No.: 10/311,392
(22) PCT Filed: May 4, 2001
(86) PCT No.: PCT/HR01/00019
§ 371 (c)(1),
(2), (4) Date: Dec. 13, 2002
(87) PCT Pub. No.: WO01/95920
PCT Pub. Date: Dec. 20, 2001

(65) Prior Publication Data
US 2004/0253322 A1 Dec. 16, 2004

(51) Int. Cl.⁷ .............................................. A61K 35/78
(52) U.S. Cl. ....................... 424/725; 424/773; 424/774; 514/770
(58) Field of Search .................. 424/725, 773, 424/774; 514/770

(56) References Cited

U.S. PATENT DOCUMENTS 4,935,580 A * 6/1990 Chao et al.

FOREIGN PATENT DOCUMENTS

WO    WO 98/19688 A1 * 5/1998
WO    WO 99/55351 A1 * 11/1999

OTHER PUBLICATIONS

Concepcion–Rosabal et al. (Zeolites (1997), vol. 19, No. 1, pp. 47–50).*
JP 59044312 (Derwent abstract XP–002182271) (1982).*

* cited by examiner

Primary Examiner—Susan D. Coe
(74) Attorney, Agent, or Firm—Katten Muchin Zavis Rosenman

(57) ABSTRACT

This invention refers to the preparation for elimination of neuropathies in diabetes. The preparation contains a combination of minerals and plant extracts. By its ionic exchange, the invention reduces considerably the process of apoptosis of nerve-cells, eliminates the process of activation of the immunologic system, and stops the immunologic reaction of auto-destruction of nerve-cells. Depositing of immunoglobulin on axons is absent, and neuropathic pain disappears. Furthermore, the preparation reduces the activity of free radicals, improves the regulation of glycemia and improves the recovery of axons which are already damaged.

58 Claims, 10 Drawing Sheets

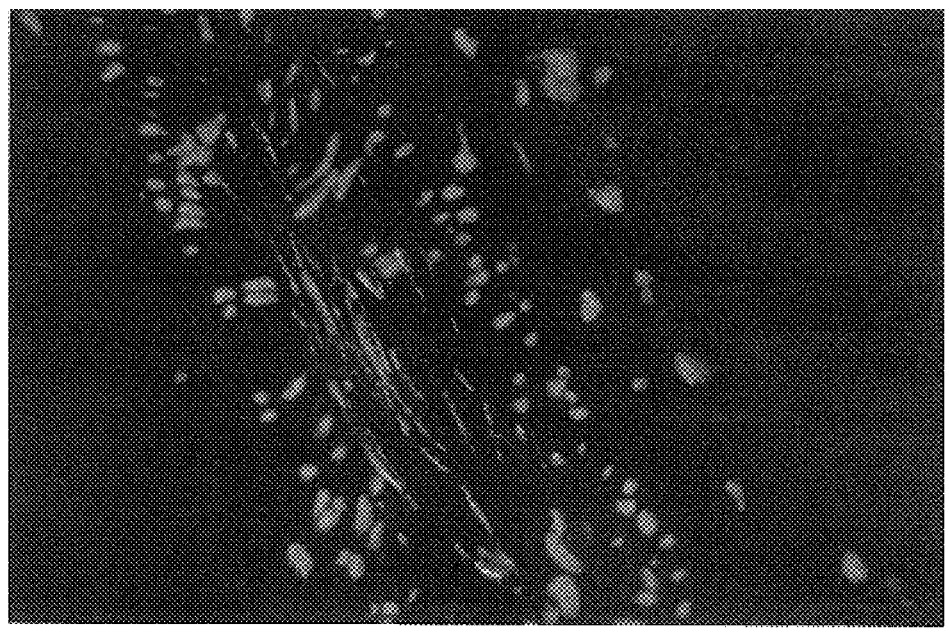
Figure 7. Cross-section through *n. ischiadicus* of diabetic mice after 180 days of the duration of the illness.
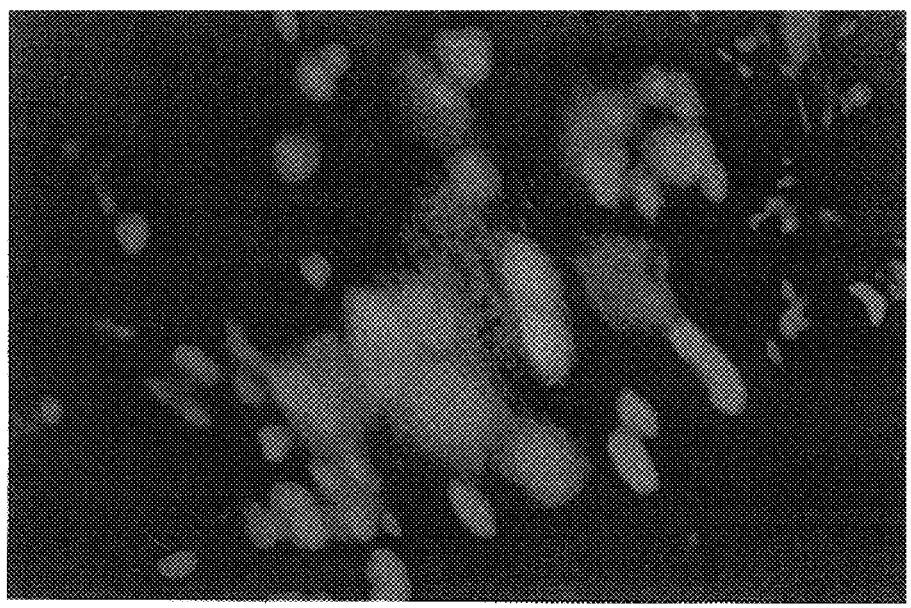
Figure 8. Cross-section through *n. ischiadicus* of diabetic mice treated by the mineral-herbal preparation after 180 days of the duration of the illness.

| GROUPS | MONTHS | | | | | | |
|---|---|---|---|---|---|---|---|
| | 0 | 1 | 2 | 3 | 4 | 5 | 6 |
| CONTROL | 34.6+1.9 | 38.7+1.9 | 39.7+2.8 | 42.5+2.0 | 40.6+4.5 | 41.3+4.2 | 40.5+3.8 |
| DIABETIC CBA | 30.7+2.9 | 25.1+1.9 | 28.2+3.4 | 25.9+4.8 | 28.6+4.3 | 28.6+3.0 | 30.5+3.2 |

FIG. 9

| GROUPS | MONTHS | | | | | | |
|---|---|---|---|---|---|---|---|
| | 0 | 1 | 2 | 3 | 4 | 5 | 6 |
| NOD | 35.1+2.5 | 34.7+3.3 | 30.1+4.4 | 28.7+4.9 | 31.4+5.4 | 31.9+4.6 | 30.5+3.2 |
| NON-DIABETIC NOD | 31.4+5.5 | 32.8+7.1 | 35.6+1.0 | 34.9+1.6 | 37.6+1.3 | 38.1+1.6 | 36.4+2.4 |

FIG. 10

| GROUPS | DAYS | | |
|---|---|---|---|
| | 7 | 90 | 180 |
| CONTROL | 2.23±0.06 | 2.15±0.06 | 2.22±0.07 |
| DIABETES | 2.2±0.07 | 2.06±0.05 | 1.97±0.12 |
| DIABETES +INVENTION | 2.17±0.06 | 2.15±0.07 | 2.24+0.1 |

FIG. 11

| GROUPS | DAYS | | |
|---|---|---|---|
| | 7 | 90 | 180 |
| NOD | 2.12±0.06 | 2.11±0.08 | 1.91±0.08* |
| NOD +INVENTION | 2.2±0.09 | 2.05±0.04 | 2.16+0.09 |

FIG. 12

| GROUPS | DAYS | | |
|---|---|---|---|
| | 7 | 90 | 180 |
| DIABETES | - | + | +++ |
| DIABETES +INVENTION | - | - | + |

FIG. 13

| GROUPS | DAYS | | |
|---|---|---|---|
| | 7 | 90 | 180 |
| NOD | + | ++ | +++ |
| NOD +INVENTION | + | + | + |

Table 7. Percentage of apoptotic bodies, and the percentage of IgG positive nerve axons in CBA mice after 6 months (180 days) of testing (n=20).

| Groups | Days | |
|---|---|---|
| | Apoptosis (%) | IgG (%) |
| Diabetes | 54-76 | 75-92 |
| Diabetes + Invention | 12-18 | 3-10 |

FIGURE 16

Table 8. Percentage of apoptotic bodies, and the percentage of IgG positive nerve axons in NOD mice after 6 months (180 days) of testing (n=20).

| Groups | Days | |
|---|---|---|
| | Apoptosis (%) | IgG (%) |
| NOD | 66-81 | 82-96 |
| NOD + invention | 7-14 | 3-8 |

INHIBITORS OF APOPTOSIS OF NERVE CELLS

FIELD OF THE INVENTION

This invention refers to the mineral-herbal preparation which is applied for prevention of the development of neuropathies in persons suffering from diabetes. By this invention, the process of apoptosis caused by accumulation of $Ca^{2+}$ ions in cytoplasm of nerve cells is stopped.

DESCRIPTION OF THE INVENTION

The technical problem which was set before the inventor, and the solution of which is presented in this patent application, consists in the invention of the mineral-herbal preparation, which is applied for prevention of the development of neuropathies in patients suffering from Diabetes mellitus, which will have the following characteristics:

1) it reduces the concentration of glucose,
2) the process of depositing of $Ca^{2+}$ ions into nerve cells can be stopped by it,
3) it stops the process of apoptosis in nerve cells stimulated by depositing of $Ca^{2+}$ ions,
4) the process of phagocytosis of apoptotic bodies is absent,
5) it stops the process of creating immunoglobulin on myelin fibres of the nerve membrane,
6) it reduces the depositing of immunoglobulin on axons,
7) it reduces the immunological destruction of axons mediated by the complement,
8) pain caused by diabetic neuropathy is absent,
9) it contains substances for elimination of free radicals,
10) it contains the daily dose of B complex vitamins,
11) it leads to ionic exchange,
12) it does not pass through villi,
13) it leads to ionic exchange through intestine-blood barrier,
14) its particles are of micron and submicron size,
15) its fragmentation is carried out in the jet mill,
16) it is mechanically treated,
17) it is chemically treated,
18) it is thermally treated,
19) the concentration of Na~ions is reduced,
20) it is enriched with Ca2~ions,
21) by mechanical treatment, the maximum capacity of the ionic exchange is achieved,
22) by thermal treatment, the maximum capacity of the ionic exchange is achieved,
23) by chemical treatment, the maximum capacity of the ionic exchange is achieved,
24) the dose in relation to the natural clinoptilolite is reduced,
25) the capacity of the ionic exchange in relation to the natural clinoptilolite is increased,
26) it is suitable for oral administration,
27) no noticeable harmful side effects appear even with large daily doses, and in case of a long-term use,
28) it is not toxic.

BRIEF DESCRIPTION OF THE DRAWINGS

FIG. 7 is a cross-section through *n. ischiadicus* of diabetic mice.

FIG. 8 is another cross-section through *n. ischiadicus* of diabetic mice.

FIG. 9 is Table 1, a table of mice body mass.

FIG. 10 is Table 2, another table of mice body mass.

FIG. 11 is Table 3, showing the concentration of $Ca^{2+}$ in mice serum.

FIG. 12 is Table 4, showing the concentration of $Ca^{2+}$ in mice serum.

FIG. 13 is Table 5, showing the presence of neuropathy in diabetic CBA mice.

FIG. 14 is Table 6, showing the presence of neuropathy in diabetic NOD mice.

FIG. 15 is Table 7, showing the percentage of apoptotic bodies in CBA mice.

FIG. 16 is Table 8, showing the percentage of apoptotic bodies in NOD mice.

TECHNICAL PROBLEM

Figure 1:
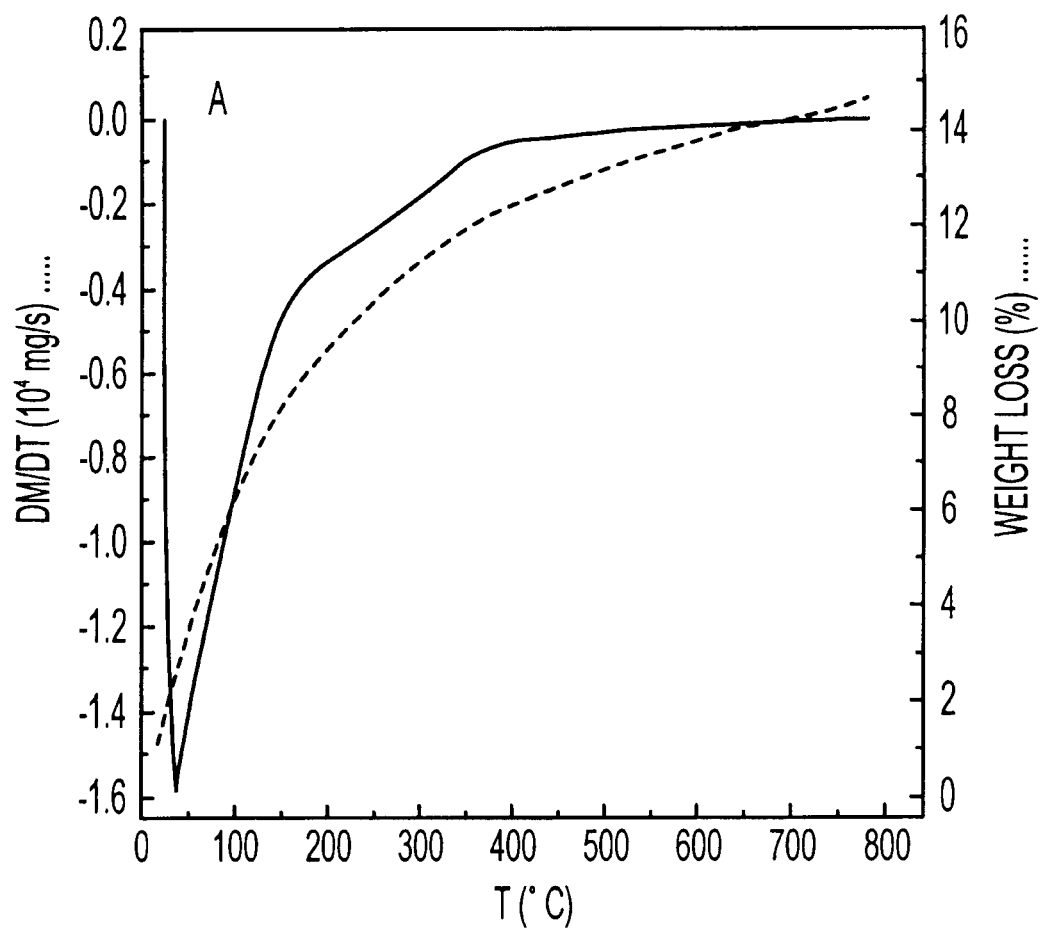
FIG. 1 a graph of the differential thermal analysis of SM clinoptilolite.
Figure 2:
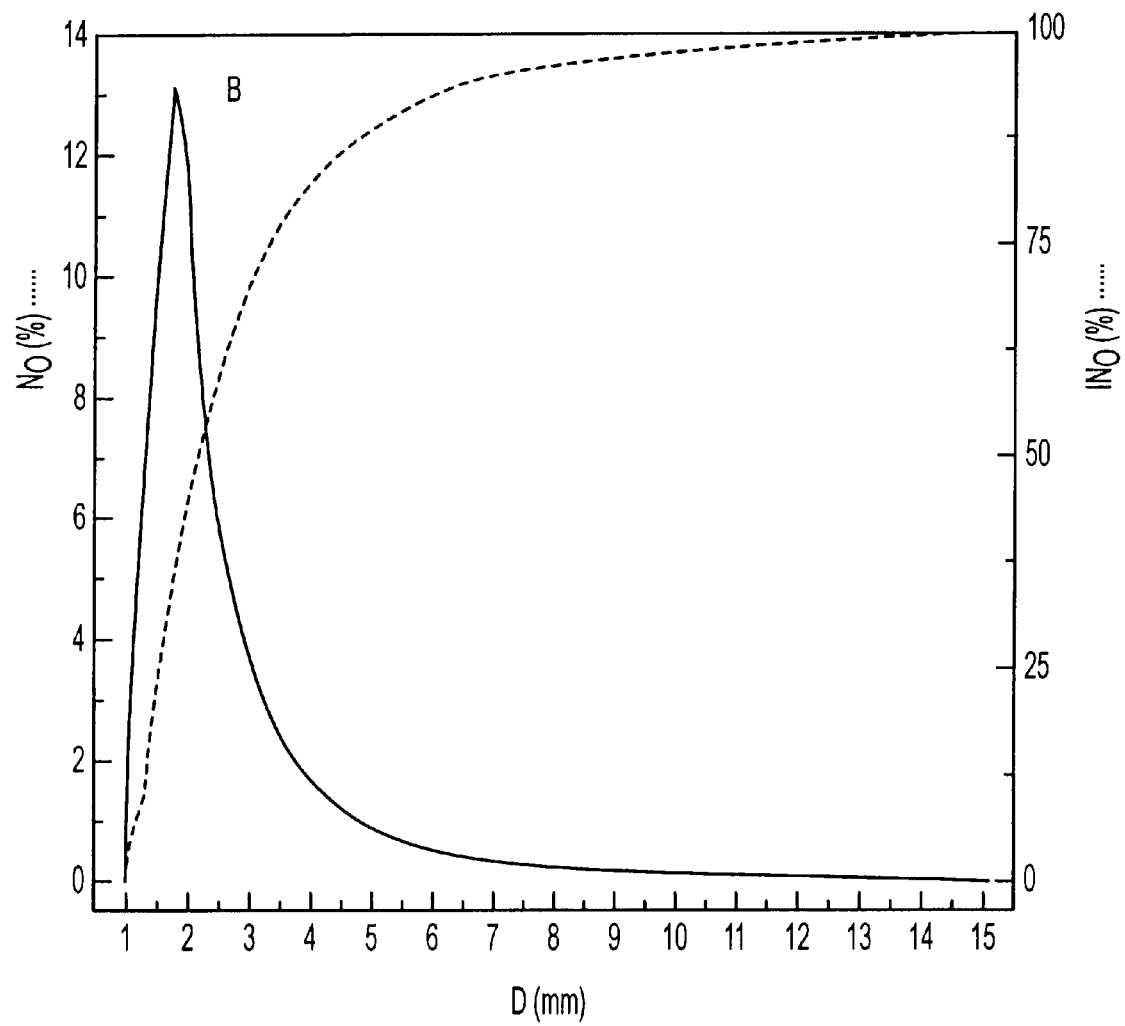
FIG. 2 is a graph of the size distribution of particles of SM clinoptilolite.

Diabetes mellitus is a hereditary metabolic disturbance, which becomes expressed under the influence of the environment factors. Its main characteristic is a relative lack of insulin, its ineffectiveness, that is, poor or no use of the hydrocarbons entered in the organism which results in the increased level of glucose in blood or hyperglycemia. Diabetes of Type I, that is, IDDM (insulin dependent diabetes mellitus) is characterized by progressive autoimmune process of destruction of f3 cells of Islets of Langerhans by T lymphocytes (Eisenbarth, G S. New Engl. J. Med. 314:1360–1368, 1986). More precisely, IDDM is the result of the destruction of beta cells mediated by CD4+and CD8+cells and the function of antigen presenting cells (APC) (Frque F., Hadzija M., et al., Proc. Natl. Acad. Sci., USA, 91:3936–3940, 1994).

NOD (non-obese diabetic) mice develop the classical picture of diabetes which is completely identical to IDDM in people (Makino S., et al., Expl. Anim. 29: 1 (1980)). Furthermore, chemical diabetes caused by alloxan in mice also develops the picture of diabetes with all the accompanying symptoms identical to the human form of diabetes of Type I (Dunn J. S., et al., Lancet II: 384–387, 1943).

The purpose of the therapy of diabetes is the normalization of the following parameters: the concentration of glucose in blood, the concentration of lipids, and the absence of glucose and acetone in urine.

The therapy is carried out in six ways: by diabetic nourishment, by physical activity, by education and self-control, by oral hypoglycemic medicaments, by exogenous insulin or by transplantation of pancreas or islets.

Insulin

Insulin is a polypeptide hormone consisting of the 51 amino acid. It is made of two polypeptide chains which are mutually connected by two disulfide bridges, and it is created in β cells of Islets of Langerhans of the pancreas, from where it is secreted into blood. Only 25% of the total insulin from the pancreas enters blood stream daily, and most of it remains stored in p cells (Huton J. C., Diabetologia 32: 271–281).

The main stimulus to secretion of insulin is glucose which concurrently stimulates the synthesis of insulin as well. Except for it, secretion is also stimulated by:

particular ingredients of food (amino acids, higher fatty acids) some gastrointestinal hormones (secretin, cholecystokinin, gastrin . . . ).

The secretion curve has a biphasic shape: a sudden short-term increase of secretion is followed by a slower, long-term secretion. The first phase corresponds to the release of the stored insulin, and in the second phase, new synthesized insulin is released.

Secretion of Insulin is Inhibited by:
somatostatin
catecholamines through β adrenergic receptors
hypothalamus through n. splanchnicus.

Insulin acts through insulin receptors which are located on the outer side of cell membranes of target organs (liver, muscles, fat tissue), so that, bound through the so-called "second messenger" in that way, it causes changes of cell enzymes (activation and inhibition) and the change of the cell membrane. Because of that, the action of insulin depends, beside on its concentration, also on the number and the affinity of insulin receptors.

Physiological Effects of Insulin:

by induction of enzymes, it stimulates the deposit of glucose in the liver in form of glycogens, inhibiting glycolysis as well it increases the synthesis of triglycerides and obstructs glucogenesis in the liver it increases the transport of glucose and amino acids into the muscle tissue where th synthesis of proteins and glycogens is increased it inhibits the hydrolysis of the stored triglycerides in the fat tissue, and activates lipase which decomposes lipoproteins.

With the lack of insulin in diabetic patients, the synthesis of proteins is reduced, and a large quantity of free amino acids is available for glucogenesis. Besides, free fatty acids pass into blood in an increased extent, and from it to the liver, where they are decomposed to acetyl-CoA by β-oxidation, and the increased quantity of acetyl-CoA cannot be used in the citric acid cycle, but acetoacetic acid is made, which leads to ketogenesis.

Oral Hypoglycemic Substances

Oral antidiabetics are a support to secretion of endogenic insulin, or they prevent the decomposition of glucose, and they are effective in the presence of at least a small quantity of insulin. By the chemical structure, they are classified as preparations of sulfonylurea, biguanides and inhibitors of glycosidase (Pickup J C, Blackwell, 1997).

Derivatives Of Sulfonylurea

Historical subclassification: preparations of "the first generation": tolbutamide, chlorpropamide preparations of "the second generation": glybenchlamyde, glyquidon, glychlaside, glypiside Activity Mechanism For achieving of the hypoglycemic effect of the derivatives of sulfonylurea, at least partly preserved production of insulin in β cells is necessary. On the molecular level, the basic mechanism of activity is the inhibition of the so-called $K^+$ channels dependent on ATP. The blockade of ATP dependent $K^+$ channels consequentially causes the increased entering of $Ca^{2+}$ into the cell which mobilizes the secretory granules with insulin according towards the cell membrane and stimulates their exocytosis.

Pharmacokinetics

After the peroral application, faster resorption of all the preparations is achieved, which mostly bind themselves to plasma proteins. They are mostly excreted by urine, and some through bile as well.

Side Effects

They cause side effects in form of gastrointestinal disturbances (anorexia, nausea), skin reactions (urticarias), cholestatic jaundice, and intolerance to alcohol. Concurrent taking with some medicaments (e.g. sulfonamides, phenylbutazone, salidylates . . . ), which repress the preparations from the connection with plasma proteins, can strengthen the hypoglycemic action of the preparations of sulfonylurea (Scheen A. J., et al., Drugs 55:225–236, 1998).

Biguanides

Among biguanides we include: metformin, buformin and fenformin.

Activity Mechanisms

The mechanism of the activity of biguanides is not quite known yet. It is supposed that those medicaments reduce the concentration of glucose in blood of diabetic patients, probably by increasing the degree of utilization of glucose in peripheral tissues, by stimulation of glycolysis, by inhibition of glyconeogenesis in liver, by reduction of the intestinal resorption of glucose, and by lowering the level of glucagon in the plasma (Pickup J. C., Blackwell, 1997; Scheen A. J., et al., Drugs 55: 225–236, 1998).

Pharmacokinetics

After the resorption in the digestive tract, biguanides are bound to plasma proteins. They are excreted by kidneys, and the halftime of semi-elimination is different depending on the preparation.

Side Effects

Side effects in form of gastrointestinal disturbances (nausea, vomiting, metal taste in the mouth) are frequent, which can also be the first sign of the most difficult side effect—lactoacidosis (disturbance of metabolism with the increase of the concentration of lactic acid in tissues and in blood). Lactoacidosis is more common in patients with the damaged function of kidneys and liver, in pregnancy, in increased consumption of alcohol.

They have a favourable therapeutic effect in obese patients. They are also used in combination with preparations of sulfonylurea and inhibitors of α-glucosidases.

α-Glucosidase Inhibitors

Among inhibitors of α-glucosidase, we include: acarbose, myglytol, voglybose, castanospermin Acarbose Activity Mechanism Acarbose is pseudotetrasaccharide of microbiological origin from the genus Actinomices. It is a competitive and reversible inhibitor of intestinal enzymes of glucoamylase, saccharase, maltase, dextrinase, as well as pancreatic amylase. Structurally, it is similar to oligosaccharides which develop by hydrolysis of starch. An acarbose molecule consists of acarviosin and a unit of glucose mutually connected by α1–14 glycoside bonds. For the inhibition of α-glycosidase, the secondary group of acarviosins is responsible, which prevents the carboxyl group of enzymes to protonate the oxygen of the glycoside bond. Thus, due to the reversible process, the hydrolysis of oligosaccharides is postponed, which reduces absorption of glucose in blood after a meal (Clissold S. P., et al., Drugs 35: 214–243, 1989).

Pharmacokinetics

After oral application, acarbose is absorbed only 1 to 4%. It metabolizes with the help of amylases of the digestive tract and intestinal bacteria.

Antidiabetic Effect

Acarbose in patients with NIDDM prevents hyperglycemia after a meal, reduces the concentration of glucose in blood and reduces the need for insulin.

Contraindications

Acarbose is contraindicated in patients with disturbances of digestion and absorption, with chronical diseases of liver, and during pregnancy and lactation.

Development of Neuropathy in Diabetes

Neuropathy is a frequent late complication in diabetes which affects somatic and autonomous nerves. Neuropathy appears in a certain percentage in diabetes Type I and in Type II (Greene D. A., et al., Diabetes Care 15: 1902–6, 1992). Peripheral nerve abnormalities in people or in animal model of diabetes are manifested by reduction of the conductibility of nerves, by shortening of axons, by reduction of the number of axons, connected with metabolic disturbance, including the changes of calcium signal. Studies carried out until now showed that the disturbance of homeostasis of Ions of calcium is a widespread occurrence in IDDM and NIDDM. The same change was noticed both, in people suffering from diabetes, and in animal models of diabetes, and that is the increase of the concentrations of $Ca^{2+}$ ions in cytosol. The increase of the concentration of calcium ions aids to the process of the natural way of dying (apoptosis) of nerve cells, but that process was shown in many other experimental models too.

The latest researches showed that "the factors from the serum" have an important role in pathogenesis of diabetic neuropathy in patients with Type I diabetes. By incubation of β cells of islets of Langerhans in conditions of the culture of tissues, when the serum of patients with Type I diabetes was added to the medium, apoptosis with β cells L.o. was connected with the increase of the concentration of-calcium ions of L type. It was also shown that neuroblastoma cells showed a reduced growth, the increase of entering of $Ca^{2+}$ ions, that is, the increased apoptosis, if they were exposed to the serum of patients suffering from Type I diabetes with neuropathies. The complement of an independent, Ca dependent induction of apoptosis of nerve cells improves the appearance of autoimmune immunoglobulins in diabetes on nerve axons.

Zeolites are a group of natural minerals of the basic structure of $AlO_4$ and $SiO_4$ tetrahedrons mutually bound by an oxygen atom. Their basic characteristic is that, by their structure, they are microcrystals with micropores of various diameters and of various composition dependant on origin. Until today, the known zeolites of natural, that is, artificial origin, are applied in industry; but also in medicine.

EXAMPLES OF REALIZATION

Natural clinoptilolite showed unfavourable chemical-ionic composition for this invention, due to a too low concentration of $Ca^{2+}$ ions. As such, it had to be submitted to the process of semi-synthesis whereby the replacement of $Na^+$ ions with $Ca^{2+}$ ions happens.

Working Example 1

Semi-synthetic Clinoptilolite

Clinoptilolite is heated to 500° C. for the purpose of eliminating of molecular water. By a screw conveyor, clinoptilolite treated in that way is in a controlled way and continuously brought to a high temperature vessel from which it is transported under pressure into a jet of compressed air with the speed of 510 m/s, so that particles of minerals accelerated in that way collide with an obstacle prepared for that purpose in order to be fragmented to the necessary size. Particles created in that way are submitted to ionic exchange in the liquid phase enriched with $Ca^{2+}$ ions by standard procedure (Breck D W, J.Chem Educ 41:678, 1964; Fedorov V A, et all, Zh Fiz Khim. 38: 1248, 1964; Wolf F, Foertig H. Kolloid Z.-Z. Polymere 206: 48, 1965; Sherry H S, Adv. Chem Ser, 101: 350, 1971; Brooke N M, Rees L V C, Adv Chem Ser. 101: 405, 1971; Barrer R M, Klinowski J Phil Trans. 285: 637, 1977). Thus prepared clinoptilolite is further used for preparation of the mineral-herbal preparation from the invention.

In order that the Ca—form of clinoptilolite be achieved, after the temperature treatment, clinoptilolite was submitted to semi-synthetic exchange in the liquid phase and enriched with $Ca^{2+}$ ions. An ionic exchange follows:

Working Example 2

Ionic Exchange

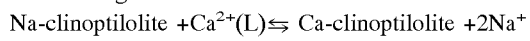

Na-clinoptilolite +$Ca^{2+}$(L)⇌ Ca-clinoptilolite +2$Na^+$

Clinoptilolite SM prepared in that way was used in preparation of the mineral-herbal preparation from this invention.

The composition of the mineral-herbal preparation includes also:

Working Example 3

Extract of Nettle Root, Stalk and Leaf

*URTICAE RADIX, HERBA ET FLOS*

*URTICA DIOICA L.*, URTICACEAE—NETTLE

The extract from the *Urtica dioica* is obtained in by standard procedure, shortly: the mixture of the nettle root, stalk and leaf, was cut into tiny pieces, and from plant substance cut in that way extract was made in 3–8 days. Extraction can be done with water, with acetone, ethanol, 70% of ethanol and 30% of water, alcohol. Solvent was removed from the extract by evaporator R-114, Buchi, Switzerland, and by a further procedure, the extract of nettle was frozen in liquid nitrogen and then lyophilized by standard procedure. The obtained powder had all the characteristics described below and used in popular medicine.

Nettle contains many minerals, calcium 490 mg %, iron 10 mg % (most than all the self-grown vegetables), a little sulfur, sodium and potassium, quite a lot of organic acids, vitamin C, depending on the season, up to 174 mg %, vitamin B1, histamine, chlorophyll, some enzymes. People have used nettle against anemia for a long time, which is also justified for anemias arisen due to the lack of iron. That is in accordance with the popular belief that nettle has a positive effect on strengthening of defense powers of the organism.

Tea from leaves of nettle stimulates the excretion of urine. For example, two week treatment increases the volume of urine and reduces the body mass. Taking nettle has a particularly favorable effect on diseases of prostate in older men. It stimulates the circulation and eliminates uric acid from the organism, so that it is recommended in case of arthritis and gout. It can help in healing of diseases of liver and bile. Popular medicine uses fresh nettle leaves. It prepares juice by pressing of fresh plant, then, tea, syrup and extract, and hot compresses are put on burns, cuts and inflamed hemorrhoids. Nettle preparations are applied externally in case of seborrhea and balding. Nettle seeds are given in case of tuberculosis and for treatment of lungs after bronchitis.

It was recently discovered that the plant contains about 5.9 mg % of proteins.

Working Example 4

*ASTRAGALUS*
*ASTRAGALI RADIX*
*ASTRAGALUS MEMBRANACEUS* (FISCH. EX LINK)
Fabaceae The extract from the *Astragalus membranaceus* is obtained in by standard procedure, shortly: the root of *astragalus* is cut to tiny pieces, and from the plant mass cut like that, extract is made in 3–8 days. Extraction can be done with water, with acetone, ethanol, 70% of ethanol and 30% of water, alcohol. Solvent was removed from the extract by evaporation (Evaporator R-114 Buchi, Switzerland), the extract of astragalus was frozen in liquid nitrogen and lyophilized by standard procedure. The obtained powder had all the characteristics described below and used in popular medicine. Thus, astragalus is spread in the territory of eastern Mediterranean and southern and western Asia.

The medicinal part of the plant are underground parts. *Astragalus* contains many active substances: Astragalosides from I to VII. Triterpene glycosides, flavonol glycosides, saponin. Tests on animals showed its immunostimulatory effect and protection of organism from the effect of toxins. It helps in illnesses of peripheral blood vessels and improves the peripheral circulation.

Its antioxidant effect was proved, that is, soothing of the consequences of the liver cirrhosis.

In popular medicine it is used for strengthening of organism, as an immunostimulator, diuretic, and in case of infections of upper respiratory tract.

Notify extracts was mixed in adequate mass ratio.

Working Example 5

Preparation of B Complex

The basic source of B complex vitamines is preparation rich in proteins, hydrocarbons, lipids, minerals, vitamins and essential amino acids.

As the basic source of vitamins of B complex was used from inactive Saccharomyces sp. a preparation rich in proteins, hydrocarbons, lipids, minerals, vitamins and essential amino acids. This preparation was used as the basic source of vitamins of B complex in the mineral-herbal preparation Except for the stated, the mineral-herbal preparation can, but need not contain other minerals too, like mordenite, montmorilonite.

Working Example 6

Analyzed by Atomic Absorption Spectroscopy SM clinoptilolite, as fine dust, is chemically treated and analyzed by atomic absorption spectroscopy. The quality and quantity of the invention is analyzed by diffractometry by x-rays on the Siemens 500° D. diffractometer of $CuK_\alpha$ radiation, in the region $2\theta=4$–$80°$.

Working Example 7

Thermogravimetry

Thermogravimetry of SM clinoptilolite, that is, the differential thermogravimetry was analyzed by the use of the device TA4000 Mettro-Toledo.

Working Example 8

Size of Particles

The size of particles of SM clinoptilolite is determined by the method of diffusion of the laser light on the device Mastersize XLB, Malven.

Working Example 9

Experimental Diabetes

Testings were made on two models of experimental diabetes.

Experimental diabetes was caused by alloxan in CBA mice, in the dose of 75 mg/kg of body weight. After the appearance of the symptoms of diabetes, 3 mice were kept in each cage.

NOD mice, which developed all the symptoms of diabetes, were taken in the experiment.

In toxicological tests, the mineral-herbal preparation was admixed to the standard food for laboratory mice.

This invention will now be shown with particular examples showing that, in case of diabetes, a syndrome is in question, and that, for a successful treatment of diabetes mellitus type I or II, it is not sufficient to apply the known medicine which has only the characteristic of a strong hypoglycemic effectiveness, but that the mineral-herbal preparation from the invention should be applied which helps the disturbed metabolism its entirety.

Working, Example 10

Determining of the Level of Apoptosis

The level of apoptosis was determined after cutting of the sample of the nerve in cryostat. To cut samples of 4 82 m, propidium iodine was added and the sample was analyzed under fluorescent microscope.

Working Example 11

Presence of IgG on Nerves

The presence of IgG on nerves was ascertained by colouring of nerves with antibodies on IgG conjugated with fluorescein.

Working Examples 12

Diabetic animals which were receiving the mineral-herbal preparation with this composition: SM clinoptilolite of 50 mg, mordenite 15 mg, montmorilonite 15 mg, extract of astragalus 5 mg, extract of nettle 11.5 mg, B1 10 $\mu$g, B2 8 $\mu$g, B6 1.25 $\mu$g, B12 0.3 $\mu$g, with all the symptoms of diabetes, with 17.3 mM/L glucose in blood. Mice were placed in metabolic cages and during 6 days the quantity of water drunk, the quantity of food eaten, of urine and feces excreted were measured. During the first three days of the application of the mineral-herbal preparation, animals did not show the reduction of the symptoms of diabetes. The same was repeated in the next three days. The concentration of glucose in blood was above 18 mM/L, and the animals drank more than 30 ml of water daily. Further therapy also did not have a positive effect on symptoms of diabetes in CBA and NOD mice either. Here should particularly be pointed out that no significant developments were made for the purpose of reducing the level of glucose, and that the symptoms of diabetes were also not reduced. During the test, mice were moderately active.

Working Example 13

Diabetic animals which were receiving the mineral-herbal preparation with this composition: clinoptilolite 180 mg, mordenite 27.5 mg, montmorilonite 22 mg, extract of astragalus 6 mg, extract of nettle 12 mg, B1 25 $\mu$g, B2 18 $\mu$g, B6 2.5 $\mu$g, B12 0.7 $\mu$g, with all the symptoms of diabetes, with 14.5 mM/L. glucose in blood. Mice were placed in metabolic cages and during 6 days the quantity of water drunk, the quantity of food eaten, of urine and feces excreted were measured. During the first three days of the application of the mineral-herbal preparation, animals did not considerably reduce the symptoms of diabetes. The same was repeated in the next three days, so that the volume of water drunk and the urine excreted was reduced by 50%. In the test of burdening with glucose, the mineral-herbal preparation did not show a hypoglycemic effect, but the curve of the assimilation of glucose was considerably more favourable in relation to untreated control mice, which is valid both for CBA diabetic mice, and for NOD diabetic mice. During the further therapy, through 6 months, the symptoms of diabetes were not eliminated, but they were considerably reduced. One should particularly point out here that for the purpose of reduction of glucose no significant developments were made, but that the symptoms of diabetes were considerably reduced. During the test, mice were moderately active.

Working Example 14

Diabetic animals which were receiving the mineral-herbal preparation with this composition: clinoptilolite 600 mg, mordenite 60 mg, montmorilonite 80 mg, extract of astragalus 11 mg, extract of nettle 9 mg, B1 3.5 µg, B2 2 µg, B6 2.5 µg, B12 2.75 µg, with all the symptoms of diabetes, with 14.7 mM/L glucose in blood. Mice were placed in metabolic cages and during 6 days the quantity of water drunk, the quantity of food eaten, of urine and feces excreted were measured. During the first three days of the application of the mineral-herbal preparation, there was a reduction of the symptoms of diabetes. The quantity of water drunk and food eaten in the group of CBA diabetic mice and in the group of NOD diabetic mice was reduced considerably. The volume of urine excreted was also reduced. In the next three days, the symptoms of diabetes returned. The concentration of glucose in blood was over 15 mM/L, and animals drank about 25 ml of water daily. The further therapy did not have a positive effect on the symptoms of diabetes either. One should particularly point out here that for the purpose of reduction of glucose no significant developments were made, and also that the symptoms of diabetes were not reduced either. During the test, mice were moderately active.

Pharmacological Data

Toxicology

No harmful toxic effects were ascertained if the animals were receiving the mineral-herbal preparation during 6 months, that is, one year.

The effect of this mineral-herbal preparation on the concentration of glucose in blood was tested in control and diabetic CBA and NOD mice. The results were compared with the group of diabetic CBA mice which were not receiving the preparation.

After 14 days, the animals were receiving the invention through a probe in the quantity of 50 to 400 mg on 25 grams of the body weight. On the 14$^{th}$ day, the zero sample of blood (25 µL) was taken from the tail vein. Mice were submitted to the test of assimilation of glucose (OGTT). During the next 2 hours, in certain periods of time, blood samples were taken and the concentration of glucose in them was determined.

Figure 3:
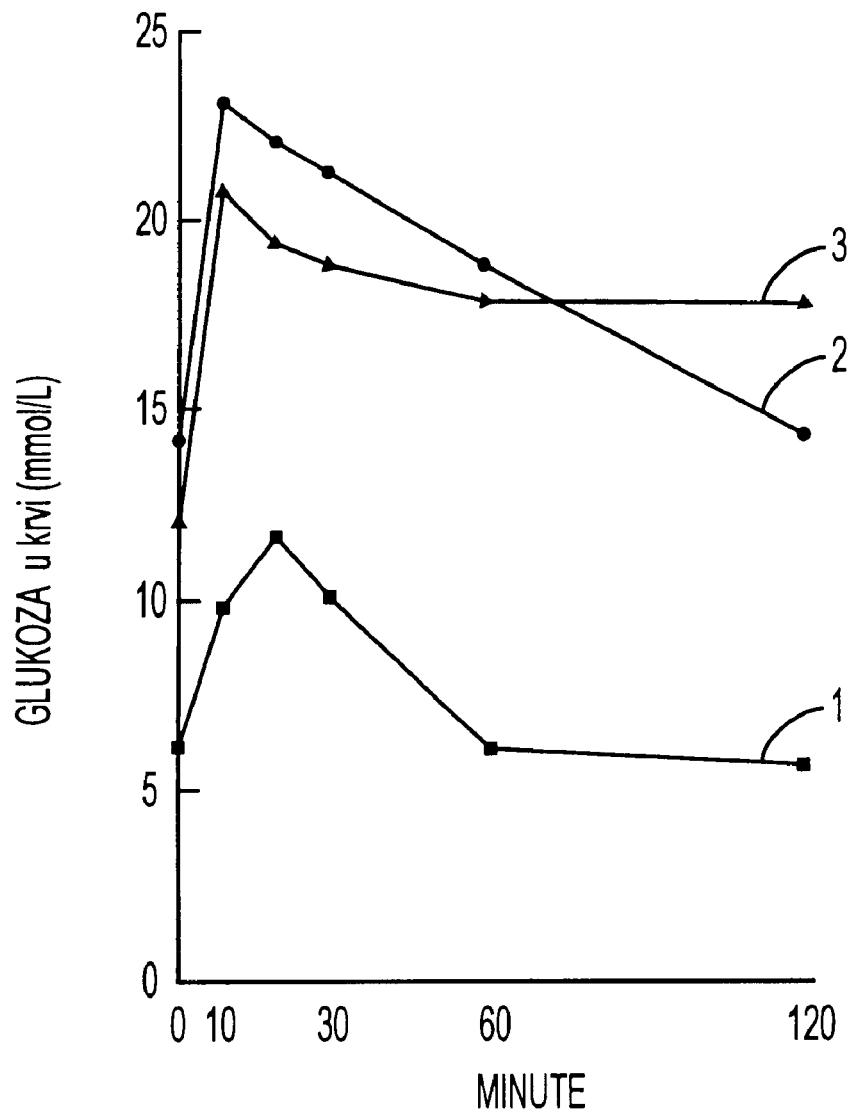
FIG. 3 is a graph of glucose concentration in diabetic CBA mice.
Figure 4:
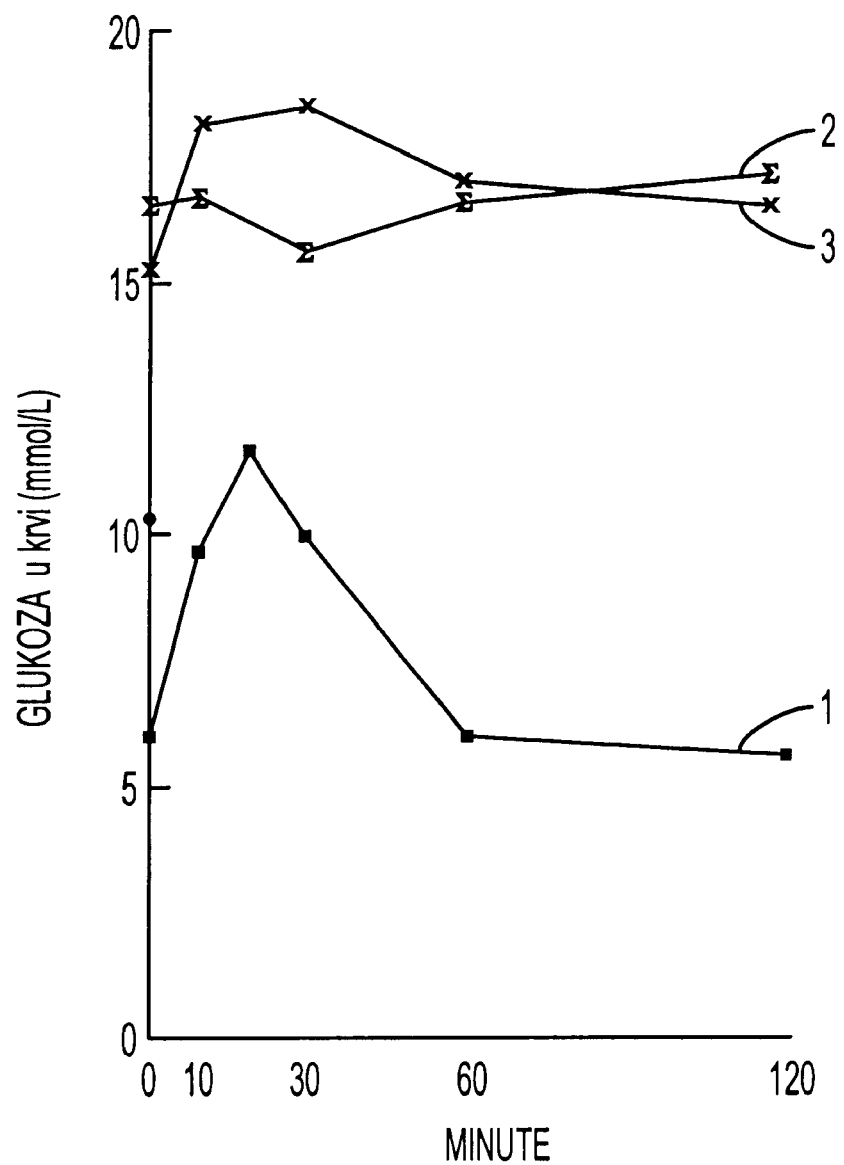
FIG. 4 is a graph of glucose concentration in diabetic NOD mice.

The results are shown in FIGS. 3 and 4. The concentration of glucose in diabetic CBA mice (10 mice per group) which were not receiving the preparation averagely amounted to 12.8±3.2 mM/L (FIG. 3). After 10, that is, 30 minutes from injecting of glucose, the concentration of glucose in peripheral blood of mice was strongly increased to values above 20 mml/L. During the next hour and a half, the concentration of glucose started to decrease, but it did not reach the values of the beginning concentration of glucose in blood (FIG. 3). However, in diabetic mice which were receiving the mineral-herbal preparation through 14 days, the concentration of glucose was considerably increased after injecting, just as it did in untreated mice. But in the following hour and a half, animals assimilated glucose more strongly and the concentration of glucose was approximately the same as the initial values of about 15 mmol/L (FIG. 3).

in NOD mice (n=12) with active autoimmune process and all the symptoms of diabetes, the concentration of glucose in blood was about 17 mmol/L. After probing of glucose in those mice, no increase of glucose in blood during the next 10, that is, 30 minutes was noticed.

But in NOD mice treated with the invention, the increase of the concentration of glucose in blood during the first 30 minutes after probing was noticed, and a slight decrease of the concentration of glucose, during the next hour and a half, towards the initial values (FIG. 4).

Results of these tests showed that the mineral-herbal preparation does not have a direct hypoglycemic effect, but that the concentration of glucose still returns to the starting hyperglycemic value.

Figure 5:
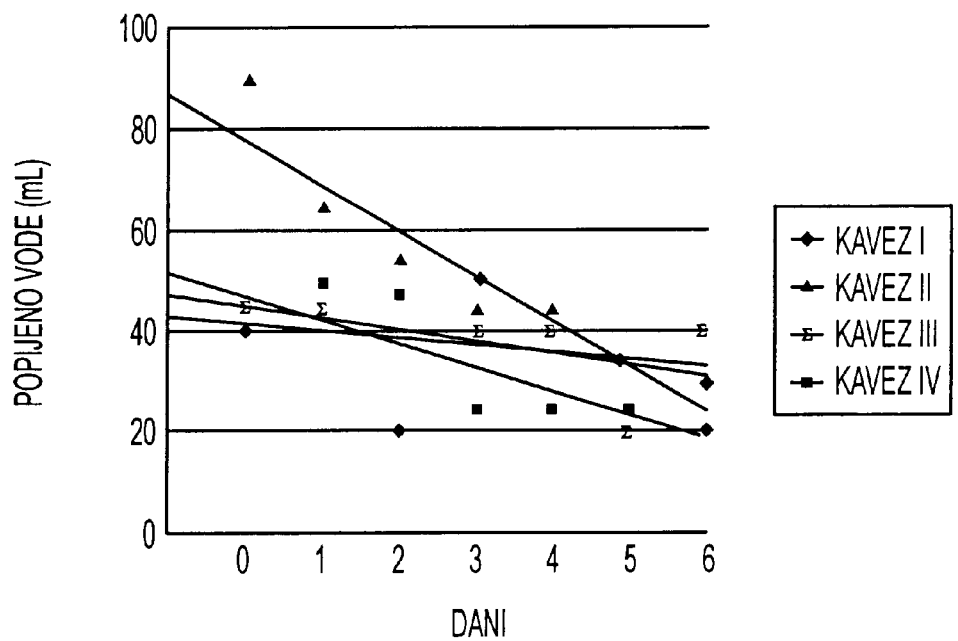
FIG. 5 is a graph of the amount of water drunk by mice.
Figure 6:
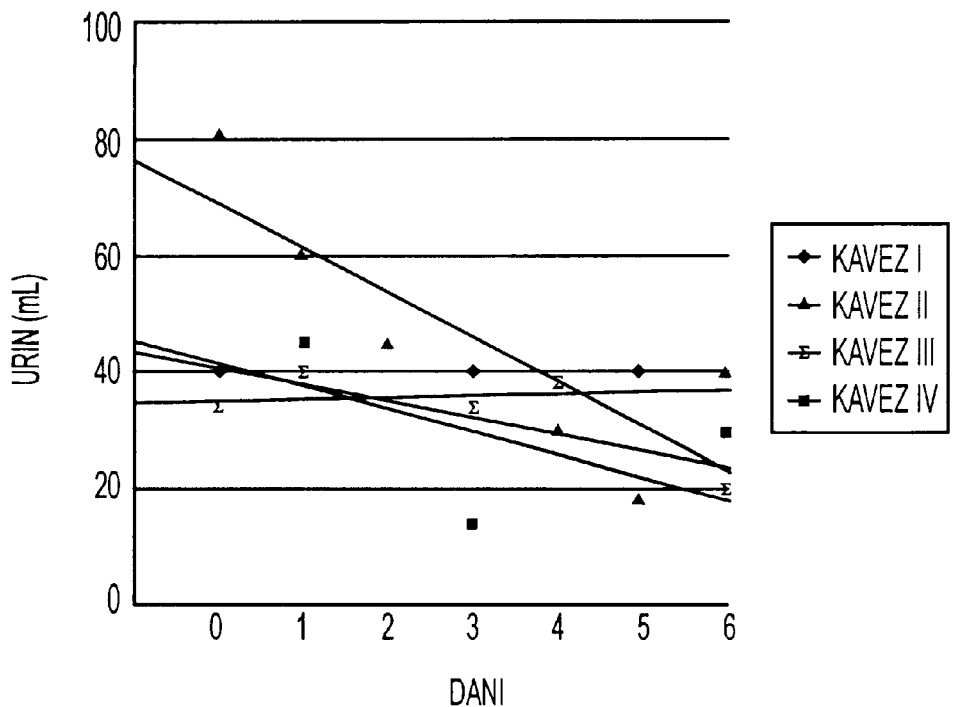
FIG. 6 is a graph of the amount of excreted urine by mice.

However, it proved that the mineral-herbal preparation has a considerable effect on other symptoms of diabetes (FIGS. 5 and 6). Thus diabetic mice which received the invention by probe through 6 days drank considerably less water during the experiment in comparison with the initial values (p<0.001) (FIG. 5).

Diabetic CBA mice which were receiving the mineral-herbal preparation for 6 days considerably reduced the volume of excreted urine during the experiment (p<0.001) (FIG. 6).

During 6 months, mice were receiving the mineral-herbal preparation together with food each day. From Table 4 is evident that the mineral-herbal preparation did not show any harmful effect because the weight of control, healthy mice was not reduced, but grew during the experiment. Thus, the body weight averagely increased from the beginning 35 grams to 40 grams.

But, in the group of CBA mice, there was a decrease of the body weight to about 26 grams during the experiment (Table 1). During the whole experiment, there was no increase of the body weight from the initial values in the group of diabetic mice (Table 1), which is a usual occurrence in case of diabetes.

During the experiment, a decrease of the body weight was noticed in the group of diabetic NOD mice (Table 2). In the beginning of the experiment, the body weight was about 35grams, while in the end of the experiment the mice weighed approximately 30 grams (table 2)

During 6 months of examining of the effect of the invention on diabetic state, the level of the concentration of calcium ions ($Ca^{2+}$) in the serum of control and diabetic mice (Table 3) was monitored. The concentration of $Ca^{2+}$ ions during the 6 months did not change in blood of diabetic CBA mice which were receiving the invention each day. But in the group of diabetic CBA mice, after the duration of illness of 6 months, there was a statistically significant decrease (p<0.05) of the concentration of $Ca^{2+}$ ions in the serum (Table 3).

In the group of control, non-diabetic NOD mice, the body weight was constantly increasing during the experiment (Table 2).

Similar results were also shown by mice with spontaneous diabetes (Table 4). The concentration of $Ca^{2+}$ions did not change in the group of diabetic NOD mice which were receiving the invention each day. A considerable reduction of the concentration of calcium ions was measured in the group of diabetic NOD mice which were not receiving the mineral-herbal preparation (p<0.05) (Table 4).

Animals from particular groups were sacrificed after 7, 90, that is 180 days. By patho-histological treatment, the level of neuropathy of the digestive tract (Tables 5 and 6) was ascertained. After 180 days, diabetic CBA mice which were not receiving the mineral-herbal preparation, developed diabetic neuropathy in 100% of cases. However, in diabetic CBA mice which were receiving the mineral-herbal preparation each day, the diabetic neuropathy was not observed (Table 5).

The same experiment was also made with diabetic NOD mice. Diabetic NOD mice develop diabetic neuropathy in 100% of cases during 6 months (Table 6). Diabetic NOD mice, which were receiving the mineral-herbal preparation during 180 days did not develop diabetic neuropathy (Table 7).

In order to check the extent of the damage of nerves, that is, to examine the presence of apoptotic bodies, on the day of sacrificing, samples of *n. ischiadicus* were taken from mice. The obtained results show that long-term diabetes has a considerable effect on the increase of the number of apoptotic bodies.

In the group of diabetic mice, the number of apoptotic bodies was about 65% (FIG. 7). In controls (healthy mice), the number of apoptotic bodies was about 7%. Diabetic mice treated with the invention did not show a considerable increase of the number of apoptotic bodies in *n. ischiadicus* (FIG. 8).

By immunofluorescent colouring, the presence of antibodies (IgG) on *nervus ischiadicus* was tested. Diabetic mice which developed all the symptoms of diabetic neuropathy showed a strong presence of IgG in *n. ischiadicus* (FIG. 7). Contrary to that, mice which were receiving the invention for 6 months did not have auto-anti-bodies on nerve axons of *n. ischiadicus* (FIG. 8).

The percentage of apoptotic bodies is statistically considerably smaller in the group of mice (CBA and NOD) treated by the invention (Table 7 and 8). Further, after colouring with anti IgG conjugated with fluorescein, the percentage of positive neurons in the group of mice treated by the invention was between 6 and 9% (Table 7 and 8).

In this patent application, specific realizations of this invention were shown. Those acquainted with this field know that various equations of this invention are possible. It should be pointed out that al such realizations of this invention are comprised by the range of patent claims that follow.

What is claimed is:

1. A mineral-herbal preparation, comprising mechanically, thermally and chemically treated natural clinoptilolite with increased concentration of $Ca^{2+}$ ions, extract of nettle leaf, root, plant, extract of astragalus and a source of B complex vitamins.

2. The mineral-herbal preparation according to claim 1, wherein the natural clinoptilolite was fragmented to micron size particles.

3. The mineral-herbal preparation according to claim 1, wherein the natural clinoptilolite was fragmented to submicron size particles.

4. The mineral-herbal preparation according to claim 1, wherein the content of clinoptilolite in the preparation of the invention is within the range from 10 to 1200 mg.

5. The mineral-herbal preparation according to claim 1, wherein the content of the extract of nettle leaf, root and plant in the preparation of the invention is within the range from 3 to 20 mg.

6. The mineral-herbal preparation according to claim 1, wherein the content of the extract of astragalus in the preparation of the invention is within the range from 1 to 20 $\mu$g.

7. The mineral-herbal preparation according to claim 1, wherein the content of vitamin B1 in the preparation of the invention is within the range from 5 to 50 $\mu$g.

8. The mineral-herbal preparation according to claim 1, wherein the content of vitamin B2 in the preparation of the invention is within the range from 0.5 to 30 $\mu$g.

9. The mineral-herbal preparation according to claim 1, wherein the content of vitamin B6 in the preparation of the invention is within the range from 0.5 to 10 $\mu$g.

10. The mineral-herbal preparation according to claim 1, wherein the content of vitamin B12 in the preparation of the invention is within the range from 0.1 to 5 $\mu$g.

11. The mineral-herbal preparation according to claim 1, further comprising montmorilonite in the quantity of 1 to 150 mg.

12. The mineral-herbal preparation according to claim 1, further comprising mordenite in the quantity of 1 to 100 mg.

13. The mineral-herbal preparation according to claim 1, wherein it contains substances for elimination of free radicals.

14. The mineral-herbal preparation according to claim 1, wherein it contains the minimum daily requirement of B complex vitamins.

15. The mineral-herbal preparation according to claim 1, compounded into an oral dosage form.

16. The mineral-herbal preparation according to claim 1, wherein the content of clinoptilolite in the preparation of the invention is within the range from 60 to 400 mg.

17. The mineral-herbal preparation according to claim 1, wherein the content of the extract of nettle leaf, root and plant in the preparation of the invention is within the range from 5 to 15 mg.

18. The mineral-herbal preparation according to claim 1, wherein the content of the extract of astragalus in the preparation of the invention is within the range from 5 to 10 $\mu$g.

19. The mineral-herbal preparation according to claim 1, wherein the content of vitamin B1 in the preparation of the invention is within the range from 10 to 40 $\mu$g.

20. The mineral-herbal preparation according to claim 1, wherein the content of vitamin B2 in the preparation of the invention is within the range from 5 to 20 $\mu$g.

21. The mineral-herbal preparation according to claim 1, wherein the content of vitamin B6 in the preparation of the invention is within the range from 2 to 8 $\mu$g.

22. The mineral-herbal preparation according to claim 1, wherein the content of vitamin B12 in the preparation of the invention is within the range from 0.1 to 2 $\mu$g.

23. The mineral-herbal preparation according to claim 1, further comprising montmorilonite in the quantity of 10 to 40 mg.

24. The mineral-herbal preparation according to claim 1, further comprising mordenite in the quantity of 5 to 50 mg.

25. A method for the treatment of diabetic neuropathy comprising administrating to a person in need thereof a therapeutically effective amount of a mineral-herbal preparation, comprising
   a) mechanically, thermally and chemically treated natural clinoptiolote with increased concentration of $Ca^{2+}$ ions;
   b) extract of nettle leaf, root, plant;
   c) extract of astragalus; and
   d) a source of B complex vitamins.

26. The method of claim 25, wherein the natural clinoptiolite is fragmented in a jet mill to micron size particles.

27. The method of claim 25, wherein the natural clinoptiolite is fragmented in the jet mill to submicron size particles.

28. The method of claim 26, wherein an angle of colliding of mineral particles in the jet mill is controlled and always the same.

29. The method of claim 27, wherein an angle of colliding of mineral particles in a jet mill is controlled and always the same.

30. The method of claim 26, wherein a speed of colliding of mineral particles in a jet mill is controlled.

31. The method of claim 27, wherein an angle of colliding of mineral particles in a jet mill is controlled.

32. The method of claim 25, wherein the content of the clinoptiolite is within the range of from 10 to 1200 mg.

33. The method of claim 25, wherein the content of the clinoptiolite is within the range of from of 60 to 400 mg.

34. The method of claim 25, wherein the content of the extract of nettle leaf, root and plant is within the range of from 3 to 20 mg.

35. The method of claim 25, wherein the content of the extract of nettle leaf, root and plant is within the range of from 5 to 15 mg.

36. The method of claim 25, wherein the content of the extract of astragalus is within the range of from 1 to 20 $\mu$g.

37. The method of claim 25, wherein the content of the extract of astragalus is within the range of from 5 to 10 $\mu$g.

38. The method of claim 25, wherein the content of vitamin B1 is within the range of from 5 to 50 $\mu$g.

39. The method of claim 25, wherein the content of vitamin B1 is within the range of from 10 to 40 $\mu$g.

40. The method of claim 25, wherein the content of vitamin B2 is within the range of from 0.5 to 30 $\mu$g.

41. The method of claim 25, wherein the content of vitamin B2 is within the range of from 5 to 20 $\mu$g.

42. The method of claim 25, wherein the content of vitamin B6 is within the range of from 0.5 to 10 $\mu$.

43. The method of claim 25, wherein the content of vitamin B6 is within the range of from 2 to 8 $\mu$g.

44. The method of claim 25, wherein the content of vitamin B12 is within the range of from 0.1 to 5 $\mu$g.

45. The method of claim 25, wherein the content of vitamin B12 is within the range of from 0.1 to 2 $\mu$g.

46. The method of claim 25, further comprising montmorilonite in the range of from about 1 to 150 mg.

47. The method of claim 25, further comprising montmorilonite in the range of from about 10 to 40 mg.

48. The method of claim 25, further comprising mordenite in the range of from about 1 to 100 mg.

49. The method of claim 25, further comprising mordenite in the range of from about 5 to 50 mg.

50. The method of claim 25 which additionally reduces the volume of urine excreted by a diabetic organism.

51. The method of claim 25 which additionally inhibits the process of apoptosis in nerve cells.

52. The method of claim 25 which additionally inhibits the process of creation of imunoglobulin on myelin fibers of nerve membrane.

53. The method of claim 25 which additionally inhibits the process of phagocytosis of apoptotic bodies.

54. The method of claim 25 which additionally reduces the deposit of immunoglobulin on myelin of nerve axons.

55. The method of claim 25 which additionally reduces immunological decomposition of nerve axons mediated by the complement.

56. The method of claim 25 which additionally eliminates pain caused by diabetic neuropathy.

57. The method of claim 25 which additionally eliminates free radicals.

58. The method of claim 25 wherein the preparation is compounded into a dosage form suitable for oral application.

* * * * *